United States Patent [19]

Kleemann et al.

[11] 4,358,615

[45] Nov. 9, 1982

[54] PROCESS FOR THE PRODUCTION OF 1-AMINO-PROPANEDIOL-(2,3) (II)

[75] Inventors: Axel Kleemann; Robert Nygren; Rudolf Wagner, all of Hanau, Fed. Rep. of Germany

[73] Assignee: Degussa Aktiengesellschaft, Frankfurt, Fed. Rep. of Germany

[21] Appl. No.: 252,459

[22] Filed: Apr. 9, 1981

[30] Foreign Application Priority Data

Apr. 12, 1980 [DE] Fed. Rep. of Germany ....... 3014109

[51] Int. Cl.$^3$ ...................... C07C 89/02; C07C 91/10
[52] U.S. Cl. ..................................... 564/475; 564/507
[58] Field of Search ............................... 564/475, 477

[56] References Cited

U.S. PATENT DOCUMENTS 2,373,199  5/1942  Schwoegler et al. ................ 564/477
3,544,632  12/1970  Haarer ................................. 564/475

FOREIGN PATENT DOCUMENTS 544944   8/1957   Canada ................................. 564/475
694992   8/1940   Fed. Rep. of Germany ...... 564/475
1941859  3/1976   Fed. Rep. of Germany ...... 564/475
158167   1/1957   Sweden ............................... 564/475
760215  10/1956   United Kingdom ................ 564/475

OTHER PUBLICATIONS

Knorr, Berichte Deutsch. Chem. Ges., vol. 32, pp. 750–757 (1899).
Baum, J. Org. Chem., vol. 27, pp. 2231–2233 (1962).
Sidgwick, "The Organic Chemistry of Nitrogen", pp. 95 & 96 (1966).

Primary Examiner—John Doll
Attorney, Agent, or Firm—Cushman, Darby & Cushman

[57] ABSTRACT

The yield of 1-amino-propanediol-2,3 is greatly increased and the process is carried out in an industrially simple manner by reacting liquid ammonia with glycidol under pressure and in the presence of a small amount of water.

33 Claims, No Drawings

PROCESS FOR THE PRODUCTION OF 1-AMINO-PROPANEDIOL-(2,3) (II)

BACKGROUND OF THE INVENTION

The production of 1-amino-propanediol-2,3 by the addition of ammonia to glycide was first described by L. Knorr and E. Knorr (Ber. deutsch. Chem. Ges. Vol. 32, pages 750–757 (1899)). The authors employed thereby one part by weight of glycidol with 100 parts by weight of 25% aqueous ammonia and then obtained after working up by distillation 1-amino-propanediol-2,3 in a yield of 44% based on the glycidol employed. The weight ratio of glycidol to aqueous ammonia (25%) = 1:100 means a mole ratio of glycidol to ammonia = 1:109.

This method of production of 1-amino-propanediol-2,3 was examined by K. Baum and W. T. Maurice (J. Org. Chem. Vol. 27, pages 2231–2233 (1962)), in which case under the same conditions they obtained yield of 68% of theory. This better yield is based on the fact that the first mentioned authors distilled the reaction product at 235°–250° C./320 mm, while the last mentioned authors carefully distilled, namely at 80°–106° C./0.1–0.15 mmHg and therewith did not cause loss through thermal decomposition.

While the last named process also brings about better yields compared to the process of Knorr (loc. cit.), the amounts of aqueous ammonia supplied to the cycle represents a considerable load in the industrial carrying out of the process.

Besides, it requires a very large reaction space because of the above-mentioned molar ratio of glycidol to ammonia, as well as a distillation plant for the concentration of the diluted aqueous ammonia solution supplied to the cycle.

The object of the invention, therefore, is the development of a process for the production of 1-amino-propanediol-2,3 in good yields and in an industrially simple manner.

SUMMARY OF THE INVENTION

It has now been found that the reaction of glycidol with ammonia in homogeneous liquid phase with good yields and without particular industrial expense can be carried out if glycidol and liquid ammonia are reacted together under such pressure that the ammonia remains liquid in the presence of a small amount of water.

In general, the molar ratio of glycidol to liquid ammonia is in the range of 1:5 to 20.

Preferably, there is a molar ratio 1:10 to 20, especially preferred is a molar ratio of 1 to 17.

Above a molar ratio of 1:20, there does not occur a considerable increase in yields; below a molar ratio of 1:5 industrially the process becomes of substantially reduced interest compared to the state of the art.

The expression "small amount of water" is relative to the previous state of the art which comprehends its very large amounts of water which are supplied to the cycle. The weight ratio of glycidol to water is in the ratio of 1:0.5 to 1:10, preferably the range is 1:1. The weight ratio of glycidol to water can even be above 10:1. However the greater this ratio is above 1:10 the lower is the space-time-yield. The pressure range is between 5 and 150 bar, preferably 20 to 90 bar.

As reaction temperature there is used 20° C. to 180° C., preferably 50° C. to 120° C.

Temperatures above and below the range mentioned are possible but temperatures below the mentioned range lead to undesirably long reaction times and those above the range to greatly increased formation of by-products.

The industrial advantage of the process of the invention, which can be carried out either discontinuously (batchwise) or continuously, is first in the great increase in yields which at the preferred ratio of glycidol to water of 1:1 leads to a previously unknown high yield.

Additionally not only the yield itself, but also the space time yield is substantially increased, namely compared to the process of Baum and Maurice (loc. cit.) around a factor of 50.

Besides the industrial expense is greatly reduced since no longer need there be recycled the increased amounts of water or must there be concentrated the very dilute aqueous ammonia solution.

It could not be foreseen that the presence of the comparatively small amount of water would increase the selectively of the reaction of glycidol and liquid ammonia under pressure.

1-Aminopropanediol-2,3 is an industrially interesting product for the production of X-ray contrast agents, inflammation arresting agents, agents against illness of birds, e.g., chickens, for analgesics and cosmetics.

Unless otherwise indicated, all parts and percentages are by weight.

The process can comprise, consist essentially of, or consist of the steps set forth with the stated materials.

The invention will be explained in more detail in connection with the following examples.

DETAILED DESCRIPTION

Experimental Apparatus

The following examples were carried out in the following experimental apparatus.

By means of two pumps, regulated amounts of the reactants were conveyed into the reactor from a supply reservoir filled with glycidol or glycidol/water and a pressure flask containing liquid ammonia. This consisted of a double walled tube wherein the outer jacket space serves, with the help of water, to bring the reaction mixture in the inner tube to the desired temperature and to carry off the heat of reaction. The reaction was carried out in liquid, homogeneous phase. The pressure needed to liquify the reaction was held through a pressure control valve at the end of the double jacketed tube. The inner tube, thus the reaction zone, had a volume of 4.2 liters. After passing through the reaction zone, the reaction mixture was relieved of pressure at the pressure control valve and led into a reservoir. From the crude product, the 1-aminopropanediol-2,3 was recovered by fractional vacuum distillation.

EXAMPLE 1

There were dosed into the above-mentioned reactor at 85° C. and 43 bar per hour 0.5 kg of glycidol, 0.5 kg of water and 1.7 kg of liquid ammonia. (Molar ratio glycidol: ammonia = 1:16.8, weight ratio of glycidol to water = 1.1). After working up the reaction product by distillation, there were obtained 0.51 kg of aminopropanediol per hour, corresponding to 83% of theory, based on the glycidol employed. Boiling point: 94° C. (0.2 Torr), purity = 99.5% (amine titration).

EXAMPLE 2

There were dosed into the above-mentioned reactor at 75° C. and 30 bar per hour 0.6 kg of glycidol, 0.6 kg of water and 1.4 kg of liquid ammonia (Molar ratio glycidol: ammonia=1:10.3, weight ratio of glycidol to water=1:1). After working up the reaction product by distillation, there were obtained 0.55 kg of aminopropanediol per hour, corresponding to 75% of theory, based on the glycidol employed.

EXAMPLE 3

There were dosed into the above-mentioned reactor at 85° C. and 43 bar per hour 0.75 kg of glycidol, 0.05 kg of water and 2.6 kg of liquid ammonia (Molar ratio glycidol: ammonia=1:17.2, weight ratio of glycidol to water 1:0.07). After working up the reaction product by distillation, there were obtained 0.64 kg of aminopropanediol per hour, corresponding to 69% of theory, based on the glycidol employed.

EXAMPLE 4

There were dosed into the above-mentioned reactor at 85° C. and 43 bar per hour 0.5 kg of glycidol, 2.0 kg of water and 1.7 kg of liquid ammonia. (Molar ratio glycidol: ammonia=1:16.8, weight ratio of glycidol to water=1:4). After working up the reaction product by distillation, there was obtained 0.49 kg of aminopropanediol per hour, corresponding to 79% of theory, based on the glycidol employed.

EXAMPLE 5

There were dosed into the above-mentioned reactor at 85° C. and 43 bar per hour 0.75 kg of glycidol, 0.25 kg of water and 2.6 kg of liquid ammonia (Molar ratio glycidol: ammonia=17:1, weight ratio of glycidol to water=1:0.3). After working up the reaction product by distillation there was obtained 0.69 kg of aminopropanediol per hour, corresponding to 74.2% of theory, based on the glycidol employed.

In Examples 2–5 also the boiling point and the purity of the product correspond to the data given in Example 1.

The entire disclosure of German priority application P No. 3014109.4-42 is hereby incorporated by reference.

What is claimed is:

1. In a process for the production of 1-aminopropanediol-2,3 by the reaction of glycidol with ammonia the improvement comprising reacting glycidol and liquid ammonia under pressure sufficient to keep the ammonia in liquid form and in the presence of water, the amount of water not being over 10 parts by weight per part by weight of glycidol.

2. A process according to claim 1 wherein the glycidol and liquid ammonia are employed in a molar ratio of 1:5 to 20.

3. A process according to claim 2 wherein the glycidol and liquid ammonia are employed in a molar ratio of 1:10 to 1:20.

4. A process according to claim 3 wherein the glycidol and liquid ammonia are employed in a molar ratio of 1:17.

5. A process according to claim 4 wherein the weight ratio of glycidol to water is from 1:0.05 to 1:10.

6. A process according to claim 3 wherein the weight ratio of glycidol to water is from 1:0.05 to 1:10.

7. A process according to claim 2 wherein the weight ratio of glycidol to water is from 1:0.05 to 1:10.

8. A process according to claim 1 wherein the weight ratio of glycidol to water is from 1:0.05 to 1:10.

9. A process according to claim 4 wherein the weight ratio of glycidol to water is 1:1.

10. A process according to claim 3 wherein the weight ratio of glycidol to water is 1:1.

11. A process according to claim 2 wherein the weight ratio to glycidol to water is 1:1.

12. A process according to claim 1 wherein the weight ratio of glycidol to water is 1:1.

13. A process according to claim 12 wherein the reaction is carried out at a pressure of 5 to 150 bar.

14. A process according to claim 11 wherein the reaction is carried out at a pressure of 5 to 150 bar.

15. A process according to claim 9 wherein the reaction is carried out at a pressure of 5 to 150 bar.

16. A process according to claim 1 wherein the reaction is carried out at a pressure of 5 to 150 bar.

17. A process according to claim 8 wherein the reaction is carried out at a pressure of 5 to 150 bar.

18. A process according to claim 12 wherein the reaction is carried out at a pressure of 20 to 90 bar.

19. A process according to claim 11 wherein the reaction is carried out at a pressure of 20 to 90 bar.

20. A process according to claim 10 wherein the reaction is carried out at a pressure of 20 to 90 bar.

21. A process according to claim 9 wherein the reaction is carried out at a pressure of 20 to 90 bar.

22. A process according to claim 8 wherein the reaction is carried out at a pressure of 20 to 90 bar.

23. A process according to claim 7 wherein the reaction is carried out at a pressure of 20 to 90 bar.

24. A process according to claim 6 wherein the reaction is carried out at a pressure of 20 to 90 bar.

25. A process according to claim 5 wherein the reaction is carried out at a pressure of 20 to 90 bar.

26. A process according to claim 4 wherein the reaction is carried out at a pressure of 20 to 90 bar.

27. A process according to claim 2 wherein the reaction is carried out at a pressure of 20 to 90 bar.

28. A process according to claim 1 wherein the reaction is carried out at a pressure of 20 to 90 bar.

29. A process according to claim 21 wherein the temperature is 50° to 120° C.

30. A process according to claim 27 wherein the temperature is 50° to 120° C.

31. A process according to claim 1 wherein the materials employed consist essentially of glycidol, water and liquid ammonia.

32. A process according to claim 1 wherein the materials employed consist of glycidol, water and liquid ammonia.

33. A process according to claim 12 wherein the glycidol and liquid ammonia are employed in a molar ratio of 1:5 to 1:20, the ratio of glycidol to water is from 1:05 to 1:10, the pressure is 5 to 150 bar and the temperature is 50° to 120° C.

* * * * *